(12) United States Patent
Jauernig et al.

(10) Patent No.: US 8,807,132 B2
(45) Date of Patent: Aug. 19, 2014

(54) DISPERSING UNIT

(75) Inventors: Jürgen Jauernig, Lörrach (DE);
Thomas Weuthen, Rudolstadt (DE);
Stefan Mackeben, Ulm (DE)

(73) Assignee: Sanofi SA, Meyrin (CH)

( * ) Notice: Subject to any disclaimer, the term of this patent is extended or adjusted under 35 U.S.C. 154(b) by 1176 days.

(21) Appl. No.: 12/223,994

(22) PCT Filed: Jan. 9, 2007

(86) PCT No.: PCT/EP2007/000129
§ 371 (c)(1),
(2), (4) Date: Apr. 29, 2009

(87) PCT Pub. No.: WO2007/096023
PCT Pub. Date: Aug. 30, 2007

(65) Prior Publication Data
US 2010/0000530 A1    Jan. 7, 2010

(30) Foreign Application Priority Data
Feb. 17, 2006  (DE) .......................... 10 2006 007 495

(51) Int. Cl.
*A61M 16/00*  (2006.01)
*A61M 15/00*  (2006.01)
*B05D 7/14*  (2006.01)
*B65D 83/06*  (2006.01)

(52) U.S. Cl.
USPC .................................................... 128/203.15

(58) Field of Classification Search
USPC ............. 128/200.11–200.23, 203.12, 203.15
See application file for complete search history.

(56) References Cited

U.S. PATENT DOCUMENTS

| | | | |
|---|---|---|---|
| 3,795,244 A | * | 3/1974 | Lax et al. ................. 128/203.15 |
| 3,838,686 A | | 10/1974 | Szekely |
| 3,938,686 A | | 2/1976 | Milligan et al. |
| 5,474,059 A | | 12/1995 | Cooper |
| 5,676,130 A | * | 10/1997 | Gupte et al. ............. 128/203.19 |
| 5,875,774 A | * | 3/1999 | Clementi et al. ......... 128/200.18 |

(Continued)

FOREIGN PATENT DOCUMENTS

| | | |
|---|---|---|
| CA | 1276848 | 11/1990 |
| CN | 1255869 | 6/2000 |

(Continued)

OTHER PUBLICATIONS

Garrod, "Glossary of the Judicial Claim Constructions in the Mechanical, Electro-mechanicla and medical devices art," PUBPAT, p. 1.*

(Continued)

*Primary Examiner* — Lynne Anderson
*Assistant Examiner* — Bradley Philips
(74) *Attorney, Agent, or Firm* — McDonnell Boehnen Hulbert & Berghoff LLP

(57) ABSTRACT

A dispersing unit for a powder inhaler comprises a mouthpiece with an annular channel for the delivery of a stream of particles. The annular channel has an axial inlet, and an axial outlet adjoined by an annular deflection chamber in which the axially incoming stream of particles is deflected to a predominantly radial direction of flow. The deflection chamber is adjoined in the axial direction by a rotation chamber with a circular peripheral wall and an axial outlet.

14 Claims, 1 Drawing Sheet

(56) References Cited

U.S. PATENT DOCUMENTS

| | | | |
|---|---|---|---|
| 5,954,047 A | 9/1999 | Armer et al. | |
| 6,286,506 B1 | 9/2001 | MacAndrew et al. | |
| 6,347,629 B1 | 2/2002 | Braithwaite et al. | |
| 6,408,846 B1 * | 6/2002 | Ohki et al. | 128/203.15 |
| 6,482,245 B2 * | 11/2002 | Brilmaker | 55/394 |
| 6,681,768 B2 * | 1/2004 | Haaije de Boer et al. | 128/203.15 |
| 7,107,987 B2 * | 9/2006 | Sundaram et al. | 128/200.23 |
| 2004/0107963 A1 | 6/2004 | Finlay et al. | |
| 2006/0096589 A1 | 5/2006 | Djupesland | |
| 2006/0254581 A1 * | 11/2006 | Genova et al. | 128/200.23 |
| 2008/0127971 A1 * | 6/2008 | King et al. | 128/203.15 |
| 2012/0174916 A1 * | 7/2012 | Kern | 128/200.21 |

FOREIGN PATENT DOCUMENTS

| | | |
|---|---|---|
| CN | 1285759 | 2/2001 |
| DE | 198 25 434 C2 | 8/1999 |
| DE | 690 12 458 T3 | 1/2000 |
| DE | 692 30 613 T2 | 12/2000 |
| DE | 696 08 561 T2 | 1/2001 |
| DE | 695 22 119 T2 | 6/2002 |
| DE | 101 29 703 A1 | 1/2003 |
| DE | 696 23 709 T2 | 1/2003 |
| DE | 696 25 219 T2 | 8/2003 |
| DE | 195 22 416 C2 | 11/2003 |
| DE | 698 11 655 T2 | 12/2003 |
| DE | 696 33 645 T2 | 10/2005 |
| EP | 1068874 A1 | 1/2001 |
| GB | 1295081 | 11/1972 |
| JP | 62-221366 | 9/1987 |
| JP | 8103499 | 4/1996 |
| JP | 2001-517499 | 10/2001 |
| JP | 2004502502 | 1/2004 |
| JP | 2004-512103 | 4/2004 |
| UA | 62916 | 1/2004 |
| WO | WO-97/11732 A1 | 4/1997 |
| WO | WO-98/26827 A | 6/1998 |
| WO | 99/15217 | 4/1999 |
| WO | 99/39761 | 8/1999 |
| WO | 9937461 A1 | 8/1999 |
| WO | 02/34320 | 5/2002 |
| WO | WO-03/090812 A | 11/2003 |
| WO | WO-2004/041338 A | 5/2004 |

OTHER PUBLICATIONS

English Translation of Chinese Office Action Issued in a Corresponding Chinese Application.
English Translation of Decision to Grant a Patent, First Sheet, Japanese Patent Application No. 2008-554616.
PatBase Express—Search Results, Abstract Document of JP8103499A.
Examination Report of Canadian Application No. 2,641,557.

* cited by examiner

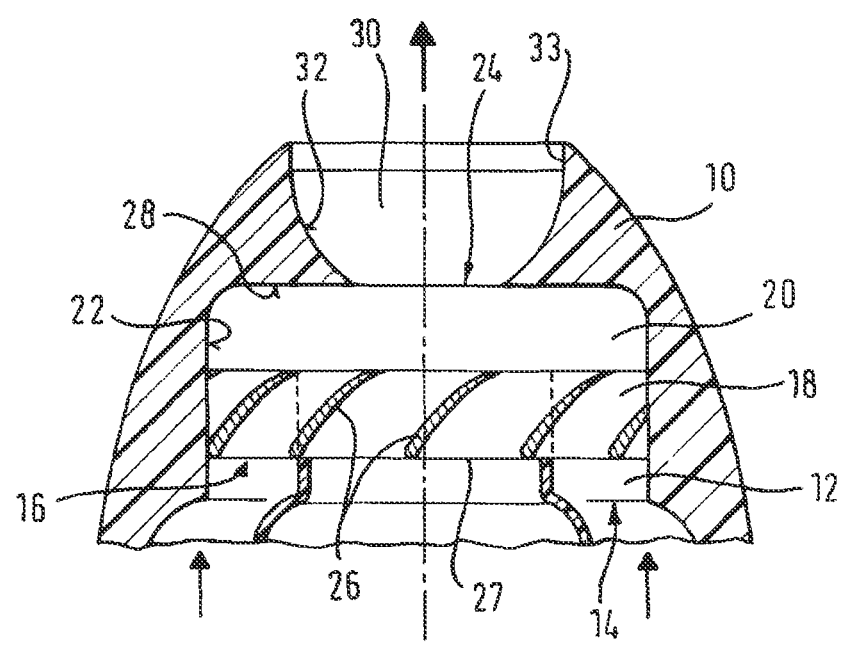

DISPERSING UNIT

CROSS-REFERENCE TO RELATED APPLICATIONS

This application is a 371 U.S. National Stage of International Application No. PCT/EP2007/000129, filed Jan. 9, 2007. This application claims the benefit of German Patent Application No. 10 2006 007 495.5, filed Feb. 17, 2006, the disclosures of which application are expressly incorporated herein by reference.

The present invention relates to a dispersing unit for a powder inhaler. Dispersing units of this type are generally known and serve to generate a dispersal of an aerosol, wherein the aerosol comprises a mixture of active agent and a carrier substance, e.g. lactose. The carrier substance mainly serves to control the physical properties of the formulation such as its flowability. In this process, the fine active agent primarily adheres to the surface of the coarse carrier substance. The adhesive forces present between carrier particles and active agent particles or between active agent particle agglomerates must be overcome during inhalation to generate a high proportion of respirable active agent particles. The energy required for this can be introduced in a dispersing unit.

In known dispersing units, impaction forces or turbulences or a combination of the two are used for the dispersion. It is also known to generate dispersion with the help of impact walls and additional supply air passages.

It is the object of the invention to provide a dispersing unit which is extremely compact in construction, is simple in construction and with which a fine particle fraction can be generated which is as high as possible without suction force loss.

This object is satisfied by the features of claim 1 and in particular by a dispersing unit having a mouthpiece in which a ring passage is provided for the supply of a particle flow. In this connection, the ring passage has an axial inlet and an axial outlet to supply the particle flow comprising a mixture of active agent and carrier substance. In accordance with the invention, a ring-shaped deflection chamber adjoins the axial outlet of the ring channel and the axially entering particle flow is deflected in a predominantly radial flow direction in it. At the same time, an acceleration of the particle flow can be achieved in this deflection chamber so that the particle flow circulates in circular form in a rotation chamber which adjoins the deflection chamber in the axial direction and has a circular peripheral wall and an axial outlet.

The particle flow supplied through the ring passage can therefore be brought into a ring-shape circulation track after exiting the deflection chamber solely by suction at the mouthpiece, with light particles, for example purely active agent particles having a particle size of less than 5 μm, being able to exit the axial outlet of the rotation chamber at an early stage due to their lower centrifugal force. On the other hand, coarser particles, for example carrier particles charged with active agent, are held longer in the rotation chamber due to their mass of inertia in which they circulate a multiple of times and impact the peripheral wall of the rotation chamber in the process, whereby the fine active agent particles additionally separate from the coarser carrier particles. All fine particles follow the airflow through the axial outlet of the rotation chamber at a slowed-down speed and are available for inhalation as a non-ballistic aerosol.

In accordance with the invention, the deflection chamber and the rotation chamber are not used for the separation of coarse particles, but a distribution between coarse and fine particles differing in the average dwell time is utilized. Coarser particles can thus also exist the rotation chamber up to the end of the inhalation procedure so that no real powder residues remain which could degrade the functionality of the inhaler or the uniformity of the dose discharge on the application of further doses.

The ring passage in accordance with the invention has an axially oriented inlet and outlet. Generally, however, the particle flow introduced into the ring passage can nevertheless also have tangential flow components.

Advantageous embodiments of the invention are described in the description, in the drawing and in the dependent claims.

In accordance with a first advantageous embodiment, guide vanes oriented obliquely to the axial direction can be arranged in the deflection chamber. The particle flow entering axially via an annular space can be deflected into a tangential flow in a simple manner using such guide vanes, with simultaneously an acceleration of the particle flow in the deflection chamber being able to be effected by the design of the deflection vanes.

It is advantageous for the guide vanes to be curved to achieve the desired deflection and acceleration effects. It can be advantageous in this process for the curvature of the guide vanes to reduce in the axial direction. The guide vane can hereby be designed in the manner of a turbine vane in order to achieve the best possible deflection and acceleration. It can also be advantageous in this connection for the guide vanes to have the profile of a wing with a curved skeleton line in section. It can also be advantageous in this connection for the guide vanes to have a rounded front edge in the region of the inlet of the deflection chamber and a rear edge with less pronounced rounding in the region of the outlet of the deflection chamber. Tests which have been made show that very good results can be achieved by such a section design.

In accordance with a further advantageous embodiment, the axial outlet of the rotation chamber is arranged centrally. Light particles can hereby exit the rotation chamber through the outlet at an early stage, whereas heavy particles circulate along the peripheral wall of the rotation chamber.

In accordance with a further advantageous embodiment, a discharge passage, which expands, adjoins the axial outlet of the rotation chamber. The expansion can be concave, whereby it is achieved that the aerosol particles exiting the outlet of the rotation chamber with relatively high speed components transversely to the direction of inhalation are slowed down in the region of the discharge passage, with the movement of the aerosol being predominantly oriented in the longitudinal direction in the outlet passage. At the same time, a slow aerosol discharge is achieved by the cross-section increase of the discharge passage so that the patient inhales a non-ballistic aerosol. The aerosol deposition in oropharyngeal region of the patient is reduced using such a mouthpiece geometry by influencing the exit direction and the exit speed. Although the aerosol exits the rotation chamber into the outlet at relatively high radial speeds, the aerosol exit speed at the end of the discharge passage is relatively low.

It can furthermore be advantageous for the discharge passage to have a circular cylindrical region in an end section at the exit side since an axial bundling of the discharge particle flow can thereby be effected. A convex design is also conceivable instead of a concave design.

The deposition of light particles from the rotation chamber can additionally be improved in that the discharge passage is sharp-edged and in particular adjoins the rotation chamber with an edge having an acute angle in cross-section.

It has also proved to be advantageous to form the transition from the circular peripheral wall to the axial outlet in the rotation chamber with a part curvature since this effects improved aerodynamics, on the one hand, and a reduced deposition of particles, on the other hand.

In the dispersing unit in accordance with the invention, no air inlet openings are provided for the supply of external air between the axial outlet of the ring passage and the outlet of the rotation chamber. It is hereby precluded that an additional suction power has to be applied to maintain the functionality of the dispersing unit, which does not benefit either the mobilization of the powder from the dispersing device nor the actual dispersing power. The deflection of the particle flow and the directed outlet into the pharynx are realized solely via geometrical implementations in accordance with the invention.

The present invention will be described in the following purely by way of example with reference to an advantageous embodiment and to the enclosed drawing.

There are shown:

FIG. 1 a partly sectioned side view of a dispersing unit.

FIG. 1 shows a dispersing unit for a powder inhaler (not shown) having a mouthpiece 10 at whose lower side a ring passage 12 is provided for the supply of a particle flow. The particle flow is generally produced by suction at the mouthpiece, for example in that a predetermined dose of active agent and carrier substance is made available in the inhaler and is then sucked into the ring passage 12 by suction at the mouthpiece.

The ring passage 12 is circumferential in the peripheral direction and has an axial inlet 14 and an axial outlet 16, with both the inlet 14 and the outlet 16 extending over the total periphery of the ring passage 12.

Adjoining the axial outlet 16 of the ring passage 12, a likewise ring-shaped deflection chamber 18 is provided which has approximately the same radial extent as the ring passage 12 and in which the axially entering particle flow is deflected into a predominantly radial direction of flow. The substantially radially directed particle flow at the outlet of the deflection chamber 18 is in this process guided into a rotation chamber 20 which has a circular peripheral wall 22 and an axial outlet 24.

As FIG. 1 shows, the outer diameters of the ring passage 12, of the deflection chamber 18 and of the rotation chamber 20 are of substantially the same size. The inner diameter of the ring passage 12 and the inner diameter of the deflection chamber 18 also correspond to one another. The inner diameter of the axial outlet 24 of the rotation chamber 20 is lower than the inner diameter of the deflection chamber 18.

To deflect the axially entering particle flow in the deflection chamber 18 into a predominantly radial flow direction and to accelerate it at the same time, a plurality of guide vanes 26 are provided in the deflection chamber 18, distributed over its periphery, and are oriented obliquely to the axial direction. Each of the guide vanes 26 extends over the total cross-section of the deflection chamber 18, with each guide vane being curved and the curvature reducing in the axial direction, i.e. being more pronounced at the inlet of the deflection chamber 18 than at the outlet. In section (longitudinal section), the guide vanes 26 have the section of a wing having a curved skeleton line. In accordance with an advantageous embodiment, the guide vanes have a rounded front edge in the region of the inlet of the deflection chamber 18 and a rear edge of less pronounced rounding in the region of the outlet of the deflection chamber 18 so that the section of the guide vanes 26 is similar to an airplane wing.

As FIG. 1 further shows, the peripheral wall 22 of the rotation chamber 20 is of circular cylindrical form and directly adjoins the outlet of the deflection chamber 18, with the axial extent of the deflection chamber 18 and of the rotation chamber 20 being approximately of equal size. At its outlet side end, the rotation chamber 20 has an end wall 28 which forms a transition between the peripheral wall 22 and the centrally arranged axial outlet 24. In this process, the transition from the circular peripheral wall 22 to the end wall 28 is curved in the region of the corner.

A discharge passage 30 whose peripheral wall 32 expands concavely adjoins the axial outlet 24 of the rotation chamber 20. The transition between the end wall 28 of the rotation chamber 20 and the peripheral wall 32 of the discharge passage 30 is, however, sharp-edged and is made with an acute angle in the embodiment shown. Furthermore, the discharge passage 30 has a circular cylindrical region 33 in its outlet side end section which extends up to the end of the discharge passage 30 and which effects an axial bundling of the discharged particle flow.

As FIG. 1 further shows, no air inlet openings for the supply of external air are provided between the inlet 14 of the ring passage 12 and the discharge passage 30.

In the use of the described dispersing unit, the patient sucks at the mouthpiece 10, whereby a particle flow is guided through the mouthpiece in the direction of the arrows shown (axial direction), said particle flow having been previously made available in a desired dose by a powder inhaler (not shown). The sucked-in particle flow is first introduced into the ring passage 12 through the inlet 14 and exits the ring passage 12 into the ring-shaped deflection chamber 18 through the ring-shaped axial outlet 16. In the deflection chamber 18, the particle flow is accelerated by the guide vanes 26, on the one hand, and deflected into a predominantly radial flow direction, on the other hand, so that the particle flow enters into the rotation chamber 20, which adjoins the deflection chamber 18 in the axial direction, approximately tangentially at the outlet of the deflection chamber 18. The particle flow rotates in the rotation chamber 20, with heavy particles circulating longer in the region of the circular peripheral wall 22 and lighter particles following the air flow and moving faster in the direction of the discharge passage 30.

The heavier particles circulating in the rotation chamber 20 initially discharge increasingly smaller (active agent) particles during their circulation due to contact with the peripheral wall 22 until these particles circulating in the rotation chamber 20 likewise follow the air flow and are then also discharged.

The described dispersing unit is made of plastic in accordance with an advantageous embodiment. It can be advantageous in this connection to make the guide vanes 26 in one piece with an insert 27, for example as an injection molded part, with the insert 27 with the guide vanes 26 molded thereon being able to be inserted into the interior of the mouthpiece 10.

The invention claimed is:

1. A dispersing unit for a powder inhaler comprising;
   a mouthpiece in which a ring passage is provided for the supply of a particle flow and comprises a ring passage axial inlet and a ring passage axial outlet,
   with the ring passage axial outlet being adjoined by a ring-shaped deflection chamber in which the axially entering particle flow is deflected into a predominantly radial flow direction and
   with a rotation chamber adjoining the deflection chamber in the axial direction, the rotation chamber having a circular peripheral wall and a centrally arranged rotation chamber axial outlet, the rotation chamber further comprising an end wall which forms a transition between the circular peripheral wall and the centrally arranged axial outlet of the rotation chamber wherein the end-wall defines a sharp edge comprising an acute angle in cross section.

2. The dispersing unit in accordance with claim 1, wherein guide vanes oriented obliquely to the axial direction are arranged in the deflection chamber.

3. The dispersing unit in accordance with claim 2, wherein the guide vanes effect an acceleration of the particle flow.

4. The dispersing unit in accordance with claim 2 wherein the guide vanes are curved, with the curvature reducing in the axial direction.

5. The dispersing unit in accordance with claim 2, wherein the guide vanes have the profile of a wing with a curved skeleton line in section.

6. The dispersing unit in accordance with claim 2, wherein the guide vanes have a rounded front edge in the region of the ring passage axial inlet of the deflection chamber and a rear edge having a less pronounced rounding in the region of the ring passage axial outlet of the deflection chamber.

7. The dispersing unit in accordance with claim 1, wherein a discharge passage, in particular a discharge passage expanding concavely, adjoins the rotation chamber axial outlet of the rotation chamber.

8. The dispersing unit in accordance with claim 7, wherein the discharge passage adjoins the rotational chamber with a sharp edge, in particular at an angle acute in cross-section.

9. The dispersing unit in accordance with claim 7, wherein the discharge passage has a circular cylindrical region in an end section at the outlet side in order to effect an axial bundling of the discharged particle flow.

10. The dispersing unit in accordance with claim 1, wherein the transition in the rotation chamber from the circular peripheral wall to the rotation chamber axial outlet is partly curved.

11. The dispersing unit in accordance with claim 1, wherein the ring passage outlet of the ring passage extends over the total periphery.

12. The dispersing unit in accordance with claim 1, wherein no air entry openings for the supply of external air are provided between the ring passage axial outlet of the ring passage and the rotation chamber outlet of the rotation chamber.

13. A dispersing unit for a powder inhaler comprising a mouthpiece in which a ring passage is provided for the supply of a particle flow and which has a ring passage axial inlet and a ring passage axial outlet, with the ring passage axial outlet being adjoined by a ring-shaped deflection chamber in which the axially entering particle flow is deflected into a predominantly radial flow direction and with a rotation chamber adjoining the deflection chamber in the axial direction, the rotation chamber having a circular peripheral wall and a rotation chamber axial outlet, wherein a plurality of guide vanes are arranged in the deflection chamber and are oriented obliquely to the axial direction, each of the guide vanes extending over the total cross-section of the deflection chamber, wherein the rotation chamber comprises an end wall that defines a sharp edge comprising an acute angle in cross-section.

14. A dispersing unit for a powder inhaler comprising;

a mouthpiece in which a ring passage is provided for the supply of a particle flow and which has a ring passage axial inlet and a ring passage axial outlet, with the ring passage axial outlet being adjoined by a ring-shaped deflection chamber in which the axially entering particle flow is deflected into a predominantly radial flow direction and with a rotation chamber adjoining the deflection chamber in the axial direction, the rotation chamber having a circular peripheral wall and a rotation chamber axial outlet, wherein the rotation chamber axial outlet is arranged centrally, a discharge passage which expands concavely and adjoins the rotation chamber axial outlet and expands concavely towards an open end of the mouthpiece, wherein the rotation chamber comprises an end wall that defines a sharp edge comprising an acute angle in cross-section.

* * * * *